(12) United States Patent
Tamano et al.

(10) Patent No.: US 11,164,112 B2
(45) Date of Patent: Nov. 2, 2021

(54) LEAVE OF ABSENCE PREDICTION SYSTEM, PREDICTION RULE LEARNING DEVICE, PREDICTION DEVICE, LEAVE OF ABSENCE PREDICTION METHOD, AND COMPUTER-READABLE RECORDING MEDIUM

(71) Applicants: NEC Corporation, Tokyo (JP); NEC Solution Innovators, Ltd., Tokyo (JP)

(72) Inventors: Hiroshi Tamano, Tokyo (JP); Atsushi Shinkai, Tokyo (JP); Masashi Nakamichi, Tokyo (JP)

(73) Assignees: NEC CORPORATION, Tokyo (JP); NEC Solution Innovators, Ltd., Tokyo (JP)

( * ) Notice: Subject to any disclaimer, the term of this patent is extended or adjusted under 35 U.S.C. 154(b) by 249 days.

(21) Appl. No.: 15/508,225

(22) PCT Filed: Sep. 2, 2015

(86) PCT No.: PCT/JP2015/004462
§ 371 (c)(1),
(2) Date: Mar. 2, 2017

(87) PCT Pub. No.: WO2016/035336
PCT Pub. Date: Mar. 10, 2016

(65) Prior Publication Data
US 2017/0286842 A1    Oct. 5, 2017

(30) Foreign Application Priority Data
Sep. 3, 2014   (JP) .............................. JP2014-179457

(51) Int. Cl.
*G06Q 10/06*     (2012.01)
*G06N 5/04*      (2006.01)
*G06Q 10/10*     (2012.01)

(52) U.S. Cl.
CPC ............... *G06Q 10/06* (2013.01); *G06N 5/04* (2013.01); *G06Q 10/1091* (2013.01)

(58) Field of Classification Search
CPC .......... G06N 5/04; G06N 20/00; G06Q 10/06; G06Q 10/1091; G06Q 50/22
See application file for complete search history.

(56) References Cited

U.S. PATENT DOCUMENTS

| 7,340,460 B1 * | 3/2008 | Kapur ................... G06F 16/955 |
| 7,792,770 B1 * | 9/2010 | Phoha .................... G06N 20/00 |
| | | 706/45 |

(Continued)

FOREIGN PATENT DOCUMENTS

WO    WO2021060970 A1 *  4/2021  ............. G06Q 10/06

OTHER PUBLICATIONS

Fujimaki et al., Factorized Asymptotic Bayesian Hidden Markov Models, Jul. 2012, International Conference on Machine Learning and https://www.profillic.com/paper/arxiv:1206.4679, p. 5-12.*

(Continued)

*Primary Examiner* — Jerry O'Connor
*Assistant Examiner* — James Webb

(57) ABSTRACT

Provided are a leave of absence prediction system and the like capable of predicting whether an employees, etc. will take a leave of absence in a predetermined time.
A leave of absence prediction system according to an aspect of the present invention is provided with: prediction rule learning means for generating a prediction rule regarding prediction of a likelihood of a leave of absence based on first attendance management information including a time-series factor concerning an employee and on information indicating presence or absence of the leave of absence concerning the employee relating to each piece of the first attendance management information, the likelihood of the leave of (Continued)

absence being a likelihood of the employee taking the leave of absence in a predetermined time; and prediction means for predicting the likelihood of the employee as a target of prediction taking the leave of absence based on second attendance management information including a time-series factor with respect to an employee as the target of prediction and on the prediction rule.

15 Claims, 10 Drawing Sheets

(56) References Cited

U.S. PATENT DOCUMENTS

| | | | | |
|---|---|---|---|---|
| 2008/0066072 A1* | 3/2008 | Yurekli | ............... | G06Q 10/06 718/104 |
| 2009/0222248 A1* | 9/2009 | Grichnik | ............... | G16H 50/20 703/11 |
| 2009/0319297 A1* | 12/2009 | Hernandez | ............ | G06Q 10/06 705/2 |
| 2014/0058801 A1* | 2/2014 | Deodhar | ............ | G06Q 10/0639 705/7.38 |
| 2014/0188768 A1* | 7/2014 | Bonissone | ............. | G06N 20/00 706/12 |
| 2014/0222741 A1 | 8/2014 | Eto et al. | | |

OTHER PUBLICATIONS

Kujipers, A prediction rule for shoulder pain related sick leave: a prospective cohort study, Dec. 6, 2006, https://link.springer.com/content/pdf/10.1186/1471-2474-7-97.pdf, p. 1-11.*

Notification of Reasons for Refusal Office Action dated Dec. 18, 2018, from the Japanese Patent Office citing references in counterpart Japanese Paten Application No. 2016-546324.

"To predict the 'mental deficiency' from the human resources information and time and attendance data 'Cydas Care'," Hiroyuki Kawashima, Impress, Inc., dated Feb. 12, 2014, Internet, [date-of-search:Dec. 5, 2018], URL:https://cloud.watch.impress.co.jp/docs/news/634746.html.

International Search Report and Written Opinion dated Oct. 6, 2015, in corresponding PCT International Application.

* cited by examiner

| EMPLOYEE | SCORE |
|---|---|
| A | 0.83 |
| D | 0.77 |
| F | 0.74 |
| C | 0.69 |
| ... | ... |

LEAVE OF ABSENCE PREDICTION SYSTEM, PREDICTION RULE LEARNING DEVICE, PREDICTION DEVICE, LEAVE OF ABSENCE PREDICTION METHOD, AND COMPUTER-READABLE RECORDING MEDIUM

CROSS-REFERENCE TO RELATED PATENT APPLICATIONS

This application is a National Stage Entry of International Application No. PCT/JP2015/004462, filed Sep. 2, 2015, which claims priority from Japanese Patent Application No. 2014-179457, filed Sep. 3, 2014. The entire contents of the above-referenced applications are expressly incorporated herein by reference.

TECHNICAL FIELD

The present invention relates to a leave of absence prediction system, a leave of absence prediction method, and a computer-readable recording medium.

BACKGROUND ART

In companies and various organizations (hereinafter referred to as "company, etc."), action for employees and members in the various organizations (hereinafter referred to as "employee, etc."), taking leaves of absence due to mental health disorders, has been problematic. If companies, etc. could take action for employees, etc. who are likely to take leaves of absence due to mental health disorders at an early stage, it is possible to reduce various economic/social losses occurring in the companies, etc., and the employees, etc. due to the leaves of absence. In other words, it is desired to predict time in which the employees, etc. take the leaves of absence due to the mental health disorders.

PTL 1 describes a mental health management device. The mental health management device described in PTL 1 determines whether the work history of an employee matches one or more determination rule indicated by determination rule data which defines a work pattern peculiar to an employee developing a psychological disorder. The mental health management device described in PTL 1 notifies a superior and the like of information with respect to an employee relating to a work history determined to match the determination rule.

PTL 2 describes a method such as managing employee behavior. In the method for managing employee behavior described in PTL 2, first, a behavior characteristic peculiar to an employee is extracted from an employee behavior history database storing behavior history of each of the employee, and the behavior characteristic is stored in an employee behavior characteristic database. In the method for managing an employee behavior of PTL 2, it is determined whether the behavior history of the employee is within the range of employee behavior characteristics relating to the employee behavior characteristic database. When the behavior history is beyond the range of the behavior characteristics, an alert message is sent to the employee.

CITATION LIST

Patent Literature

[PTL 1] Japanese Unexamined Patent Application Laid-Open No. 2008-242702A

[PTL 2] Japanese Unexamined Patent Application Laid-Open No. 2011-123579A

SUMMARY OF INVENTION

Technical Problem

PTLs 1 and 2 describe prediction of the likelihood of employees, etc. taking a leave of absence due to a mental health disorder. However, PTLs 1 and 2 do not mention prediction of time in which the employee, etc. will take the leave of absence. According to the technologies described in PTLs 1 and 2, it is difficult to predict the time in which the employee, etc. or the like will take the leave of absence due to the mental health disorder.

The present invention was accomplished in order to solve the above-described problems with a principal object to provide such as a leave of absence prediction system capable of predicting whether an employee, etc. will take a leave of absence in a predetermined time.

Solution to Problem

A leave of absence prediction system in one aspect of the present invention includes: prediction rule learning means for generating a prediction rule regarding prediction of a likelihood of a leave of absence based on first attendance management information including a time-series factor concerning an employee and on information indicating presence or absence of the leave of absence concerning the employee relating to each piece of the first attendance management information, the likelihood of the leave of absence being a likelihood of the employee taking the leave of absence in a predetermined time; and prediction means for predicting the likelihood of the employee as a target of prediction taking the leave of absence based on second attendance management information including a time-series factor with respect to an employee as the target of prediction and on the prediction rule.

A leave of absence prediction method in one aspect of the present invention includes: generating a prediction rule regarding prediction of a likelihood of a leave of absence based on first attendance management information including a time-series factor concerning an employee and on information indicating presence or absence of the leave of absence concerning the employee relating to each piece of the first attendance management information, the likelihood of the leave of absence being a likelihood of the employee taking the leave of absence in a predetermined time; and predicting the likelihood of the employee as a target of prediction taking the leave of absence based on second attendance management information including a time-series factor with respect to an employee as the target of prediction and on the prediction rule.

A computer-readable recording medium in one aspect of the present invention stores a program in a non-transitory manner, the program allowing a computer to execute: processing of generating a prediction rule concerning prediction of a likelihood of a leave of absence based on first attendance management information including a time-series factor concerning an employee and on information indicating presence or absence of the leave of absence concerning the employee relating to each item of the first attendance management information, the likelihood of the leave of absence being a likelihood of the employee taking the leave of absence in a predetermined time; and processing of predicting the likelihood of the employee as an target of prediction taking the leave of absence based on second attendance management information including a time-series factor with respect to an employee as the target of prediction and on the prediction rule.

A prediction rule learning device in one aspect of the present invention includes prediction rule learning means for generating a prediction rule regarding prediction of a likelihood of a leave of absence based on first attendance management information including a time-series factor concerning an employee and on information indicating presence or absence of a leave of absence concerning the employee relating to each piece of the first attendance management information, the likelihood of a leave of absence being a likelihood of the employee taking the leave of absence in a predetermined time.

A prediction device in one aspect of the present invention includes prediction means for predicting, a likelihood of an employee as a target of prediction taking a leave of absence based on second attendance management information including a time-series factor with respect to the employee as the target of prediction and on a prediction rule concerning prediction of a likelihood of the leave of absence, the likelihood of the leave of absence being a likelihood of an employee taking the leave of absence in a predetermined time.

Advantageous Effects of Invention

In accordance with the present invention, it is possible to provide a leave of absence prediction system or the like capable of predicting whether employees, etc. will take a leave of absence in a predetermined time.

DESCRIPTION OF EMBODIMENTS

Each example embodiment of the present invention will be described with reference to the accompanying drawings. In each example embodiment of the present invention, each component of each device exhibits a block in a functional unit.

Figure 11:
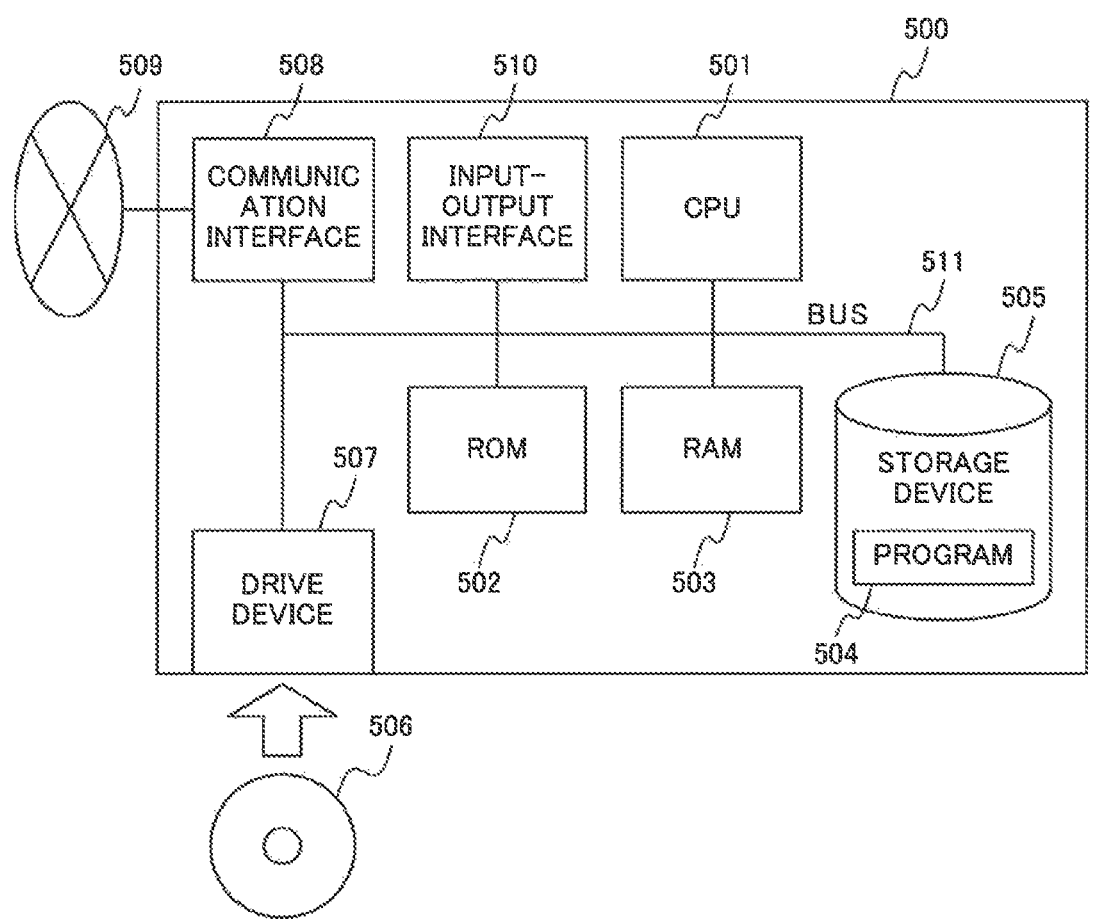
FIG. 11 is a diagram illustrating one configuration example of an information-processing device that implements a leave of absence prediction device and the like in each example embodiment of the present invention.

Each component of each device can be implemented by any combination of such an information processing device 500 as illustrated in FIG. 11 and software. The information processing device 500 includes the following configuration as an example.

CPU (Central Processing Unit) 501
ROM (Read Only Memory) 502
RAM (Ramdom Access Memory) 503
Program 504 loaded into RAM 503
Storage device 505 storing program 504
Drive device 507 that reads and writes recording medium 506
Communication interface 508 connected to communication network 509
Input-output interface 510 through which data is input and output
Bus 511 through which components are connected to each other There are various alternative examples of a method for implementing each device. For example, each device can be implemented as a dedicated device. Each device can be implemented by a combination of plural devices.

First Example Embodiment

Figure 1:
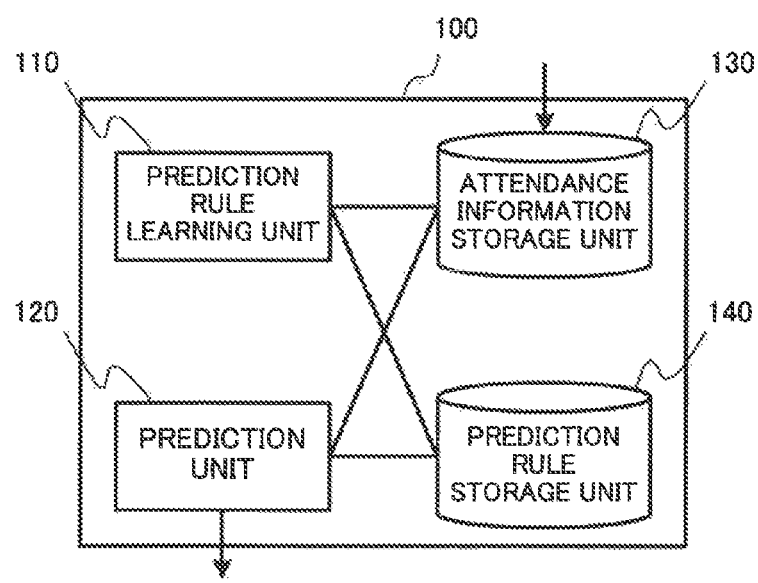
FIG. 1 is a diagram illustrating the configuration of a leave of absence prediction device in a first example embodiment of the present invention.
Figure 2:
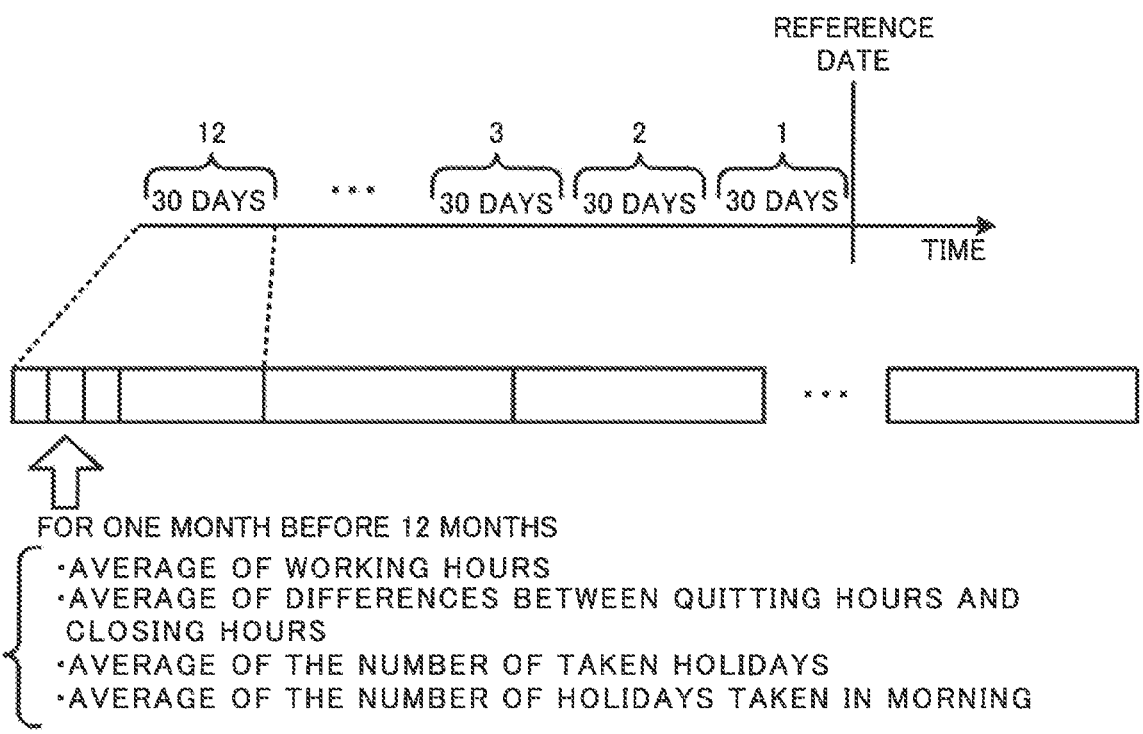
FIG. 2 is a diagram illustrating an example of attendance management information used in the leave of absence prediction device in the first example embodiment of the present invention.
Figure 3:
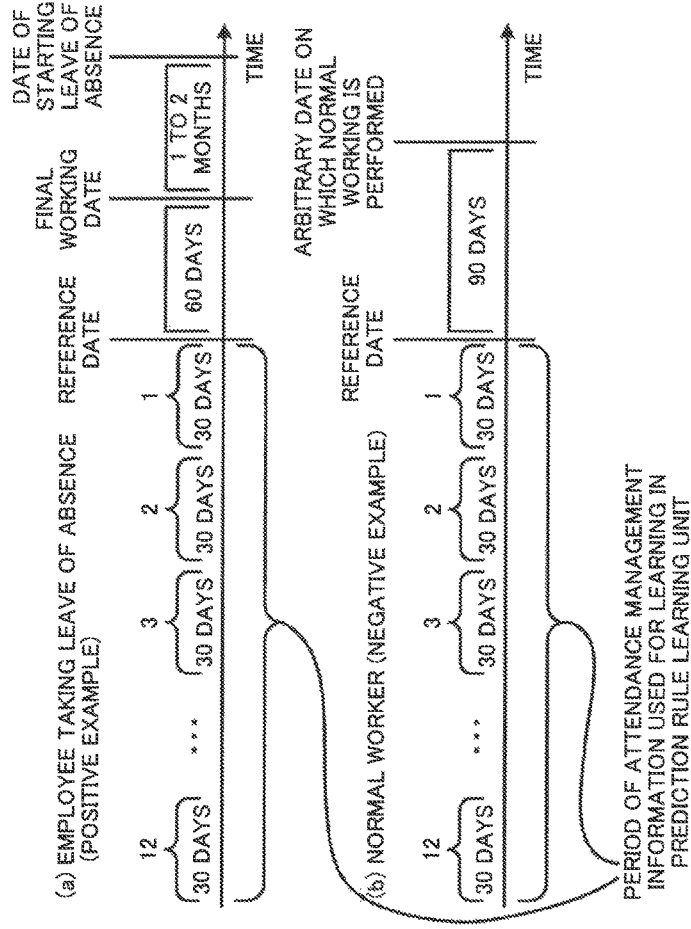
FIG. 3 is a diagram illustrating an example of attendance management information concerning an employee taking a leave of absence and a normal worker, used in the leave of absence prediction device in the first example embodiment of the present invention.
Figure 4:
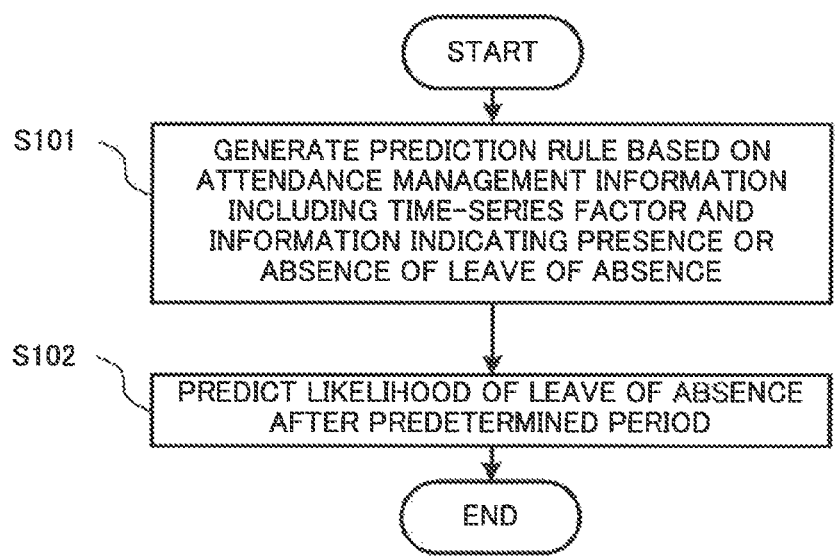
FIG. 4 is a flowchart representing the operation of the leave of absence prediction device in the first example embodiment of the present invention.
Figure 5:
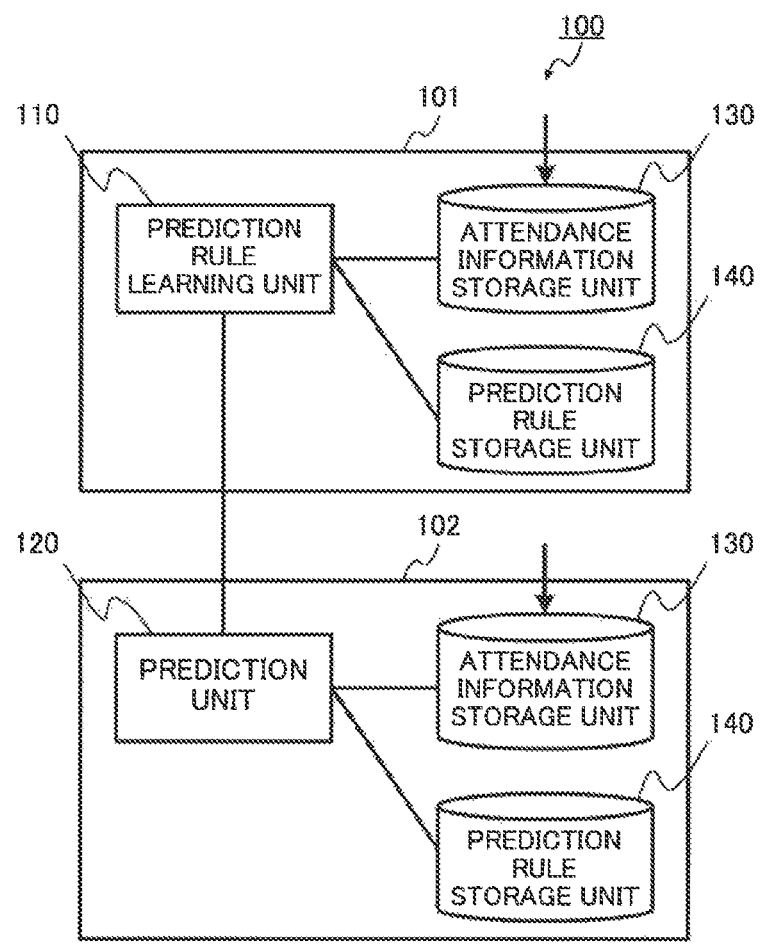
FIG. 5 is a diagram illustrating one configuration example of the leave of absence prediction device in the first example embodiment of the present invention.

First, a first example embodiment of the present invention will be described. FIG. 1 is a diagram illustrating a leave of absence prediction system in the first example embodiment of the present invention. FIG. 2 is a diagram illustrating an example of attendance management information used in the leave of absence prediction device in the first example embodiment of the present invention. FIG. 3 is a diagram illustrating an example of attendance management information concerning an employee taking a leave of absence and a normal worker, used in the leave of absence prediction device in the first example embodiment of the present invention. FIG. 4 is a flowchart indicating the operation of the leave of absence prediction device in the first example embodiment of the present invention. FIG. 5 is a diagram illustrating one configuration example of the leave of absence prediction device in the first example embodiment of the present invention.

A leave of absence prediction system 100 in the first example embodiment of the present invention includes a prediction rule learning unit 110 and a prediction unit 120, as illustrated in FIG. 1. The prediction rule learning unit 110 generates a prediction rule concerning prediction of likelihood of a leave of absence, which is the likelihood of employee taking a leave of absence in a predetermined time, based on first attendance management information including a time-series factor of employees and information indicating presence or absence of the leave of absence relating to each of the employee with respect to the first attendance management information. The prediction unit 120 predicts likelihood of target employee for prediction to take the leave of absence in a predetermined time based on second attendance management information including a time-series factor with respect to the target employee for prediction and the prediction rule. In this case, the predetermined time indicates a future time point after any period following a time point at which the prediction will be carried out.

Further, the leave of absence prediction system 100 in the present example embodiment may include an attendance information storage unit 130 and a prediction rule storage unit 140. The attendance information storage unit 130 stores the attendance management information that is used for generating the prediction rule described above and for predicting the likelihood of a leave of absence. The prediction rule storage unit 140 stores the prediction rule generated in the prediction rule learning unit 110. The prediction rule that is stored is read out by the prediction unit 120, and used for predicting the likelihood of a leave of absence.

The details of the leave of absence prediction system 100 in the present example embodiment will be described. In the present example embodiment, the first or second attendance management information is one or more items of information concerning attendance of an employee, etc. in a company, etc. The attendance management information includes, for example, information such as working hours, a difference between the time of leaving an office and the time of close of business, overtime hours, situations of taking a holiday including a half-holiday such as a holiday only in the morning or a holiday only in the afternoon, a day of the week on which a holiday is taken, or the presence or absence of holiday work. The attendance related information is not limited to such information directly representing the attendance of the employee, etc. as described above, and may include any kind of information that can influence the attendance of the employee, etc. The kind of the information included in the attendance management information is set as appropriate according to, e.g., a technique used in the prediction rule learning unit 110 or the prediction unit 120 or required prediction accuracy.

In the present example embodiment, the first or second attendance management information includes a time-series factor. In other words, the first or second work management information in the present example embodiment includes information concerning attendance in plural days, or information concerning attendance in any period. The period or the like of the information concerning the attendance included in the attendance management information may be appropriately set as needed.

The first or second attendance management information in the present example embodiment is generated from the information concerning the attendance described above, in a form suitable for the generation of the prediction rule in the prediction rule learning unit 110 and for the prediction in the prediction unit 120. The attendance management information in the present example embodiment is represented as, for example, a feature vector representing the information described above.

An example of the attendance management information including the first or second attendance management information in the present example embodiment will be described with reference to FIG. 2. In the present example embodiment, the first or second attendance management information can be represented in, for example, a similar form. Thus, in the present example embodiment, features that are common to both items of the first and second attendance management information are collectively described as the attendance management information. The attendance management information in the present example embodiment is represented as, for example, a feature vector obtained by calculating the statistics of information concerning the attendance in any periods according to the particular periods and by concatenating plural feature amounts calculated according to the periods. In other words, in such a case, the elements of the feature vector representing the attendance management information represent the individual statistics of the information concerning the attendance in the any periods. In the example illustrated in FIG. 2, the attendance management information is represented as a vector obtained by calculating the statistics of four items of information concerning attendance for 12 months, every 1 month (30 days), and by concatenating the calculated twelve statistics. The four items of information concerning the attendance are the average of working hours, the average of differences between the time of leaving an office and the time of close of business, the average of the numbers of taken holidays, and the average of the numbers of holidays taken in the morning, as illustrated in FIG. 2. In other words, the example illustrated in FIG. 2 represents a 48-dimensional vector.

In the work management information, for example, averages of items of information concerning attendance, such as working hours in any period (a period of certain one month in the case of FIG. 2), differences between the time of leaving an office and the time of close of business, the numbers of taken holidays, and the numbers of holidays taken only in the morning are used as statistics. As the statistic, information other than the described items of information can be used as needed. Such statistics are not limited to the averages of the information concerning attendance. For example, values concerning other statistics such as dispersion are used as such statistics, as needed. Each of the feature amounts included in the first or second work management information may be, for example, a value in a predetermined range, or a value such as a binary value or a ternary value.

Subsequently, the details of each component of the leave of absence prediction system 100 in the present example embodiment will be described.

First, the prediction rule learning unit 110 will be described. The prediction rule learning unit 110 performs learning on the basis of the first attendance management information and the information indicating presence or absence of the leave of absence relating to an employee corresponding to each item of the first attendance management information, and generates the prediction rule. The prediction rule learning unit 110 may use, for example, heterogeneous mixture learning including FAB inference (Factorized Asymptotic Bayesian Inference) and the like, and other known machine learning techniques when learning attendance management information and the like. The heterogeneous mixture learning technique is disclosed in, for example, U.S. Unexamined Patent Publication No. US 2014/0222741 A1 and the like.

The attendance management information and the information indicating the presence or absence of a leave of absence concerning each item of the attendance management information can be stored in the attendance information storage unit 130.

The first attendance management information is classified into attendance management information concerning an employee, etc. taking a leave of absence or the like (hereinafter referred to as "employee taking leave of absence") and attendance management information concerning an employee, etc. working as normal without taking a leave of absence or the like (hereinafter referred to as "normal worker"), on the basis of the information indicating presence or absence of a leave of absence. In other words, the first attendance management information is associated with information regarding whether the employees, etc. regarding each item of the first attendance management information has taken a leave of absence. FIG. 3 is a diagram illustrating an example of the first attendance management information.

The first attendance management information concerning an employee taking leave of absence used in the prediction rule learning unit 110 is attendance management information determined by the method described above or the like with a date, as a reference date, prior to a predetermined period from a date on which the employee taking leave of absence started the leave of absence (hereinafter referred to as "starting date of leave of absence"). In such a case, the predetermined time described above is considered to be the same as, for example, a period in which the likelihood of a leave of absence will be predicted by the prediction unit 120 described later. As an example, when the predetermined period is two months, the first attendance management information is attendance management information determined with, as the reference date, a date two months prior to a date on which the employee taking leave of absence started the leave of absence. In such a case, the prediction unit 120 predicts the likelihood of the leave of absence after two months.

The starting date of a leave of absence is not limited to a date set by the work rule of the company, etc., and may be a date on which an employee taking leave of absence stops going to the company, etc., or a date on which the employee taking leave of absence last goes to the company, etc. (last attendance date). In other words, a date on which the employee taking leave of absence stops going to the company is selected as the starting date of the leave of absence, as appropriate. In the example of FIG. 3, the first attendance management information concerning an employee taking leave of absence illustrated in (a) uses a date, as a reference date, 60 days prior to a date on which the employee taking leave of absence stops going to the company.

The attendance management information regarding a normal worker used in the prediction rule learning unit 110 is attendance management information determined by the method described above with any date on which normal working is performed as the reference date, for example. It is preferable that the normal worker regarding the attendance management information normally works for a period at least not less than a predetermined period from the end of the period included in the attendance management information regarding the normal worker. In other words, it is preferable that a date at least prior to not less than a predetermined period from the date on which the normal worker is confirmed to work normally (for example, a date to which a predetermined time with respect to the employee taking leave of absence is dated back any period) is selected as a reference date. This is because the attendance management information regarding the normal worker may be inappropriate as attendance management information regarding the normal worker in case the normal worker takes a leave of absence in the predetermined period. Therefore, the attendance management information regarding the normal worker used in the prediction rule learning unit 110 may be attendance management information that is obtained using a date, as a reference date, prior to not less than a predetermined period from the date on which normal working is performed. In such a manner, it is ensured that the employee, etc. regarding the attendance management information has worked normally for a period at least not less than a predetermined period from the end of the period included in the attendance management information used in the prediction rule learning unit 110. The attendance manager regarding the normal worker in FIG. 3 is an example of attendance management information obtained using a date, as the reference date, prior to not less than a predetermined period from any date on which normal working is performed. In the example of FIG. 3, with respect to the first attendance management information concerning the normal worker illustrated in (b), 90 days prior to any date on which normal working is performed is set as the reference date.

The prediction rule learning unit 110 generates the prediction rule by learning the difference between the patterns of the items of attendance management information corresponding to the employee taking the leave of absence and the normal worker. The prediction rule learning unit 110 may generate the prediction rule capable of distinguish the difference between the items of the attendance management information of the employee taking leave of absence and the normal worker at a point prior to a predetermined period from a date on which an employee starts taking a leave of absence. In other words, the prediction rule learning unit 110 can generate the prediction rule capable of determining whether a state of attendance is peculiar to a person taking a leave of absence at a point prior to a predetermined period from an absence period, for example, by using the first attendance management information described above. The prediction rule learning unit 110 generates the prediction rules by using one or more items of the first attendance management information regarding the employee taking a leave of absence and the normal worker respectively.

The prediction rule is generated in a form in accordance with a technique used in the prediction rule learning unit 110. As an example, when the prediction rule learning unit 110 uses a linear classifier, the prediction rule is represented in the form of a linear function by which the space of the feature vector regarding attendance management information is separated based on the presence or absence of the likelihood of taking a leave of absence in a predetermined time.

The validity of the prediction rule generated by the prediction rule learning unit 110 is confirmed based on, for example, the first attendance management information by the prediction unit 120 described later. In other words, the prediction unit 120 predicts, on the basis of the generated prediction rule and the first attendance management information, the likelihood of taking a leave of absence from the information. The validity of the prediction rule is confirmed by confirming whether the result matches with the presence or absence of a leave of absence taken by the employee, etc. regarding the first attendance management information.

The prediction rule learning unit 110 can generate, for example, a plurality of the prediction rules having different internal parameters on the basis of the first attendance management information and the information indicating presence or absence of a leave of absence concerning each item of the first attendance management information. In such a case, the prediction unit 120 may confirm which of the plural prediction rules is suitable for prediction by using the first attendance management information, in a manner similar to the confirmation of the validity described above.

Next, the prediction unit 120 will be described. The prediction unit 120 predicts the likelihood of the employee, etc. taking a leave of absence in a predetermined time because of, for example, a mental health problem. The prediction unit 120 predicts the likelihood of the employee, etc. as the target of determination taking a leave of absence in a predetermined time by applying the second attendance management information of the employee, etc. as the target of determination to the prediction rule generated by the prediction rule learning unit 110. As an example, when the prediction rule is represented as the linear classifier, the prediction unit 120 predicts the likelihood of the leave of absence by determining that a feature vector representing the second attendance management information belongs to which of feature vector spaces classified by the linear classifier. As described above, the predetermined time indicates a future time point which is an arbitrary period such as, for example, one month or two months, after a time point at which prediction will be carried out. In other words, the prediction unit 120 predicts the likelihood of the employees, etc. taking a leave of absence in the predetermined time, which is the future time point, on the basis of the second attendance management information of the employees, etc. until the time point at which the prediction will be carried out.

The leave of absence as the target of the prediction described above is not limited to a leave of absence in the work rule or the like of the company, etc., but may include a date on which the employee, etc. stops going to the company, etc. Alternatively, the leave of absence as the target of the prediction described above includes the last attendance date before the leave of absence of the employees, etc. In other words, the prediction unit 120 can also predict a likelihood that the last attendance date of the employee, etc. is included in a predetermined time.

The form of the second attendance management information used for prediction in the prediction unit 120 is intended to be similar to, for example, the form of the first attendance management information used for generating the prediction rule in the prediction rule learning unit 110, as described above. The second attendance management information differs from the first attendance management information in that the presence or absence of the employee, etc. related to the second attendance management information taking a leave of absence is unclear (the likelihood of the leave of absence is predicted by the prediction unit 120).

As described above, the prediction rule learning unit 110 generates the prediction rule by using, as the first attendance management information concerning an employee taking leave of absence, the first attendance management information with a date, as a reference date, prior to a predetermined period from a date on which the employee taking a leave of absence started the leave of absence. The prediction unit 120 can determine whether the second attendance management information of the employee, etc. as the target of determination matches (or the degree of the matching) with the state of the attendance of the employee taking leave of absence at a point prior to a predetermined period from the period of the leave of absence by using the prediction rule. Accordingly, the prediction unit 120 can predict the likelihood of the employee, etc. as the target of determination taking a leave of absence in a predetermined time.

The prediction unit 120 may determine whether the employee, etc. takes a leave of absence in a predetermined time, as a specific method for predicting the likelihood of the employee, etc. as the target of determination taking the leave of absence in the predetermined time. The prediction unit 120 may also determine the degree of the likelihood of the employee, etc. taking a leave of absence in a predetermined time, as another specific method for predicting the likelihood of the employee, etc. as the target of determination taking the leave of absence in the predetermined time. In this case, for example, the prediction unit 120 may convert the likelihood of the leave of absence into a numeric on the basis of an arbitrary criterion, and can represent the likelihood as the numeric.

When the prediction rule is represented as a linear classifier, the prediction unit 120 can determine the presence or absence of the likelihood of the employee, etc. taking a leave of absence in a predetermined time by applying the attendance management information of the employee, etc. as the target of determination to the linear classifier. The likelihood of the leave of absence in the predetermined time (or the degree of the likelihood) is predicted based on a relationship between the attendance management information and the linear classifier (for example, a distance between the attendance management information and a discriminant surface defined by the linear classifier in the feature vector spaces). The linear classifier defines a boundary surface (a boundary line in the case of two dimensions) between an employee, etc. who may take a leave of absence and an employees, etc. working as normal. In other words, each of the degree of the likelihood of taking a leave of absence and the degree of the likelihood of working normally is 50% on the boundary surface. Either the degree of the likelihood of the leave of absence or the degree of the likelihood of the normal working is increased with increasing a distance from the boundary surface.

Next, an example of the operation of the leave of absence prediction system 100 will now be described with reference to FIG. 4.

First, the prediction rule learning unit 110 generates the prediction rule (step S101). When generating the prediction rule, the prediction rule learning unit 110 reads out the attendance management information stored in the attendance information storage unit 130 and the information indicating the presence or absence of a leave of absence with respect to each of employees, etc. from the attendance information storage unit 130, and uses them. The prediction rule learning unit 110 stores the prediction rule, which is generated, in the prediction rule storage unit 140.

Then, the prediction unit 120 predicts the likelihood of an employee as the target of prediction taking a leave of absence in a predetermined time, by using the attendance management information with respect to the employee as the target of prediction including a time-series factor and the prediction rule generated in step S101 (step S102). In the prediction, the prediction unit 120 reads the attendance management information including the time-series factor with respect to the employee as the target of prediction from the attendance information storage unit 130, and uses the information. Further, the prediction unit 120 reads the prediction rule from the prediction rule storage unit 140 and uses the rule.

The leave of absence prediction system 100 in the present example embodiment generates the prediction rule by learning the attendance management information including a time-series factor of employees, etc., as described above. Then, the leave of absence prediction system 100 in the present example embodiment predicts the likelihood of an employee as the target of prediction taking a leave of absence in a predetermined time by using the prediction rule. The leave of absence prediction system 100 in the present example embodiment may determine the situation of attendance in a period prior to a predetermined period in which the employer, etc. takes a leave of absence, by generating the prediction rule with the use of the attendance management information including the time-series factor of the employees, etc. Accordingly, the leave of absence prediction system 100 in the present example embodiment may predict a period in which the employee, etc. takes a leave of absence.

In addition, a company, etc. may recognize, in advance, the likelihood of the presence or absence of an employee, etc. taking a leave of absence, and a period in which the leave of absence will be taken when there is a possibility of a leave of absence, by using the leave of absence prediction system 100 in the present example embodiment. Accordingly, it may become possible for the companies, etc. to take action for avoiding the leave of absence in accordance with the period in which the employees, etc. is predicted to take the leave of absence. In other words, both the company, etc. and the employee, etc. predicted to take the leave of absence may reduce various losses including economic losses caused by the leave of absence, by using the leave of absence prediction system 100 in the present example embodiment.

Configurations and Application Examples of Leave of Absence Prediction System

Various examples of the leave of absence prediction system 100 in the present example embodiment are conceivable as specific configurations.

As an example, in the leave of absence prediction system 100, the prediction rule learning unit 110 and the prediction unit 120 can be implemented as devices separated from each other, as illustrated in FIG. 5. In other words, the leave of absence prediction system 100 can be implemented as a system including a prediction rule learning device 101 and a prediction device 102. The devices may have a configuration in which the devices are physically separated from each other, and are connected via any kinds of wired or wireless communication network.

In addition, there may be a configuration such that both the attendance information storage unit 130 and the prediction rule storage unit 140 are included in one of the devices and are connected to the other device via the communication network. Alternatively, the attendance information storage unit 130 and the prediction rule storage unit 140 are included in each device. In this case, there may be a configuration such that the attendance information storage unit 130 and the prediction rule storage unit 140 store information which is required in each of the devices. FIG. 5 illustrates the configuration in which the attendance information storage unit 130 and the prediction rule storage unit 140 are included in each device.

Further, in such a case, there may be a configuration such that the leave of absence prediction system 100 may include a plurality of the prediction devices 120 with respect to the single prediction rule learning device 110. In this case, the single prediction rule learning device 110 and the plural prediction devices 120 are connected to each other via any kinds of communication network. Such a configuration may enable, for example, provision of service in which a business operator possessing the prediction rule learning device 110 generates the prediction rule for another business operator possessing each of the plurality of the prediction devices 120.

In the present example embodiment, the leave of absence prediction system 100 is described as a system that predicts the likelihood of an employee, etc. in a company, etc. taking a leave of absence in a predetermined time. However, the leave of absence prediction system 100 in the present example embodiment can also be applied to other fields. For example, the leave of absence prediction system 100 in the present example embodiment can predict the likelihood of a student or the like being absent (absent for a long period of time) from a school or the like in a predetermined time because of a mental health problem. In other words, "likelihood of an employee, etc. taking leave of absence in predetermined time" may be considered to encompass "likelihood of a student being absent in predetermined time" in the present example embodiment. The leave of absence prediction system 100 in the present example embodiment may also be used for predicting the likelihood of occurrence of some kind of event in a future predetermined time.

The specific configurations and application examples of the leave of absence prediction system 100 in the present example embodiment described above can be similarly applied to leave of absence prediction systems in each example embodiment described later.

Second Example Embodiment

Figure 6A:
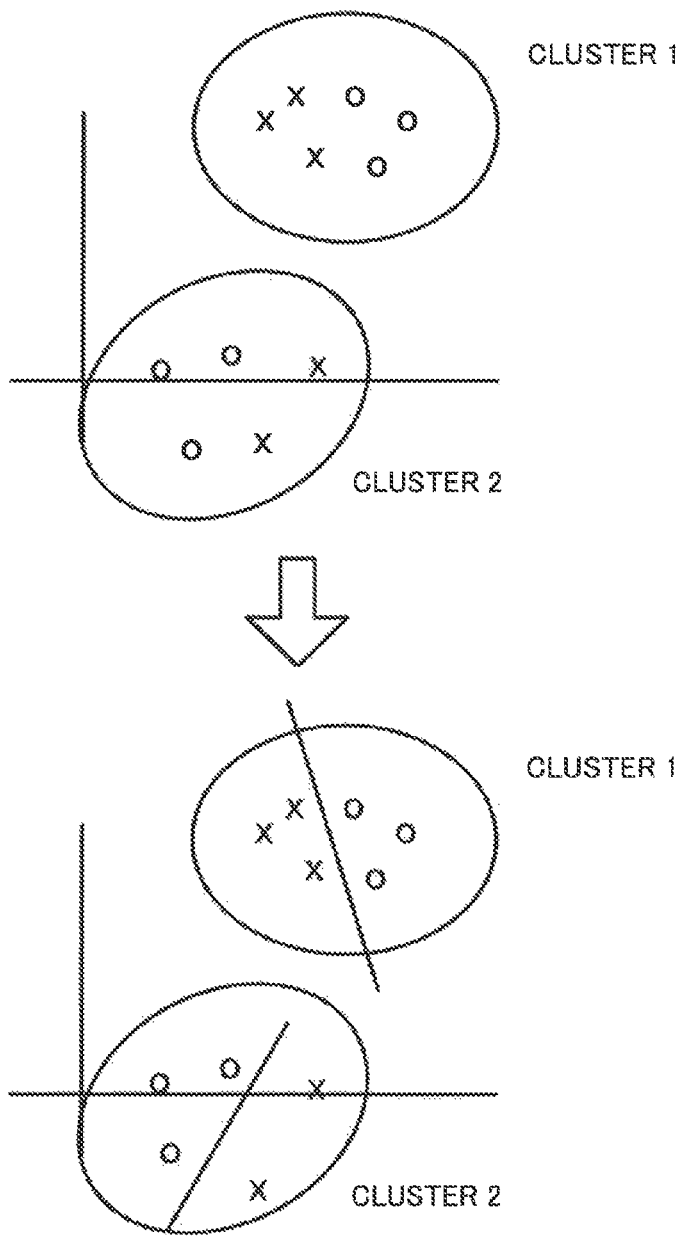
FIG. 6A illustrates an example in the case of generating a prediction rule in a prediction rule learning unit included in a leave of absence prediction device in a second example embodiment of the present invention.
Figure 6B:
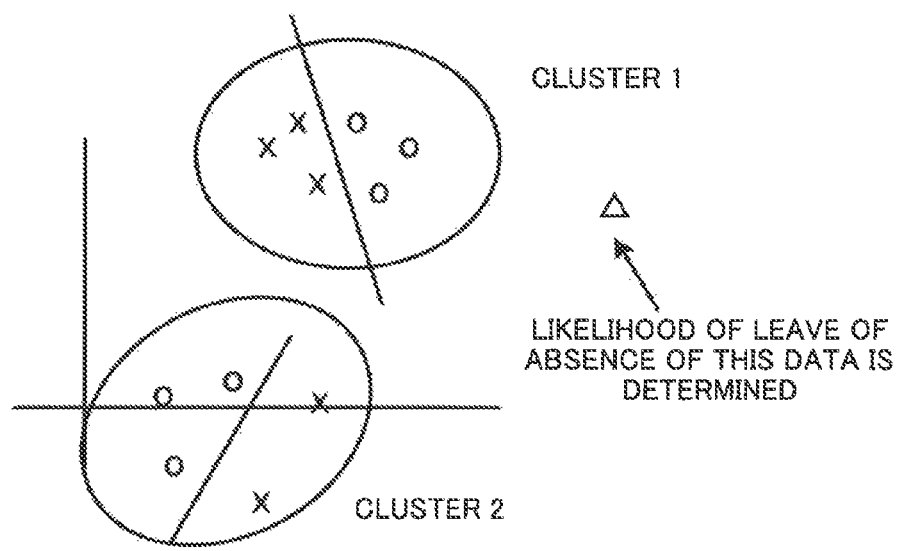
FIG. 6B illustrates an example in the case of prediction in a prediction unit included in the leave of absence prediction device in the second example embodiment of the present invention.

Subsequently, a second example embodiment of the present invention will be described. FIG. 6A illustrates an example in the case of generating a prediction rule in a prediction rule learning unit 110 included in a leave of absence prediction system in the second example embodiment of the present invention. FIG. 6B illustrates an example in the case of prediction in a prediction unit 120 included in the leave of absence prediction system in the second example embodiment of the present invention.

The configuration of the leave of absence prediction system 100 in the present example embodiment can be the same as that of the leave of absence prediction system 100 in the first example embodiment of the present invention. In the leave of absence prediction system 100 in the present example embodiment, the prediction rule learning unit 110 generates prediction rules according to employees, etc. having common properties. In the leave of absence prediction system 100 in the present example embodiment, the prediction unit 120 selects a prediction rule according to an employee, etc. as the target of prediction from the prediction rules generated according to the employees, etc. having the common properties, and predicts the likelihood of a leave of absence in a predetermined time.

The leave of absence prediction system 100 in the present example embodiment differs from the leave of absence prediction system 100 in the first example embodiment of the present invention of the present invention in view of the points described above. In other words, the leave of absence prediction system 100 in the present example embodiment classifies the first attendance management information of employees, etc. into clusters having common properties to generate the prediction rules and to predict the likelihood of a leave of absence in a predetermined time.

In the present example embodiment, the employees, etc. having the common properties are, for example, employees, etc. considered to have similar tendencies for a factor included in the first or the second attendance management information. In other words, for example, employees, etc. in which information regarding attendance included in the first or second attendance management information satisfies predetermined conditions can be regarded as the employees, etc. having the common properties in the leave of absence prediction system 100 in the present example embodiment. In this case, the information regarding attendance includes, for example, overtime hours, the number of taken holidays, the number of holidays taken on a specific day of week, or the like.

In the present example embodiment, as an example, it is determined whether employees, etc. related to the attendance management information have common properties, based on a distance between the feature vector spaces of feature vectors representing first or second attendance management information. In other words, it is determined that employees related to the first or second attendance management information in which the distance is within a predetermined range (the distance is in a short range and tendencies of the attendance are considered to be similar to each other) have common properties.

As another example, the employees, etc. having the common properties are employees, etc. having similar attributes as the target of prediction of a leave of absence, for example. In this case, the attributes of the employees, etc. are, for example, the ages, positions, duties, presence or absence of past leaves of absence, or the like of the employees, etc. as the target of prediction of a leave of absence.

In the present example embodiment, the prediction rule learning unit 110 may generate the prediction rules according to employees having common properties by an arbitrary technique. As an example, the prediction rule learning unit 110 may generate the prediction rules (for example, the discriminants) in accordance with the employees, etc. having common properties, and a decision tree representing association between first attendance management information and each of the prediction rule by using the heterogeneous mixture learning technique described above.

In this case, the prediction unit 120 selects any of the prediction rules generated in accordance with each of the employees, etc. having the common properties to be used on the basis of the second attendance management information of the employees, etc. as the target of prediction by using the decision tree described above. The prediction unit 120 predicts the likelihood of the employees, etc. as the target for prediction taking a leave of absence in a predetermined time by using the selected prediction rule.

As another example, the prediction rule learning unit 110 may carry out clustering of the first attendance management information of employees, etc., which is the learned data, and may generate a prediction rule for each of the cluster on the basis of the first attendance management information and the like of employees, etc. included in each of the cluster, as illustrated in FIG. 6A. In this case, the prediction rule learning unit 110 may use, for example, K-means or the like as a technique for carrying out the clustering of the learned data. In the example illustrated in FIG. 6A, the prediction rule learning unit 110 carries out the clustering of the first attendance management information into clusters 1 and 2, and generates a discriminant as the prediction rule for each of the cluster.

In this case, the prediction unit 120 selects a prediction rule from the prediction rules generated for each of the employees, etc. having the common properties in accordance with the second attendance management information of an employees, etc. as the target for prediction, and predicts the likelihood of a leave of absence in a predetermined time, as illustrated in FIG. 6B. In other words, the prediction unit 120 selects a cluster at the shortest distance from the feature vector representing the second attendance management information of the employees, etc. as the target of prediction. As the distance between the feature vector and the cluster, for example, a distance between the feature vector and the center of a cluster can be used. Then, the prediction unit 120 predicts the likelihood of the employees, etc. taking a leave of absence in a predetermined time by using the prediction rule generated for the selected cluster. In the example illustrated in FIG. 6B, the prediction unit 120 selects the cluster 1 for data with respect to the second attendance management information represented by a triangle mark. The prediction unit 120 then predicts the likelihood of a leave of absence regarding the second attendance management information by using a discriminant for the cluster 1.

As described above, the prediction rule learning unit 110 generates the prediction rules in accordance with each of the employees, etc. having common properties in the leave of absence prediction system 100 in the present example embodiment. In the leave of absence prediction system 100 in the present example embodiment, the prediction unit 120 selects the prediction rule with respect to an employee as the target of prediction from prediction rules generated for each of the employees, etc. having the common properties, and predicts the likelihood of a leave of absence in a predetermined time. The prediction unit 120 can enhance the accuracy of prediction of the likelihood of an employees, etc. taking a leave of absence, since the prediction rule learning unit 110 generates the prediction rules in accordance with the employees, etc. having the common properties.

The leave of absence prediction system 100 of the present example embodiment may have a configuration such that the likelihood of an employees, etc. taking a leave of absence can be predicted based on the prediction rules generated in accordance with the employees, etc. having common properties, without specifying a period in which the employees, etc. will take the leave of absence.

Third Example Embodiment

Figure 7:
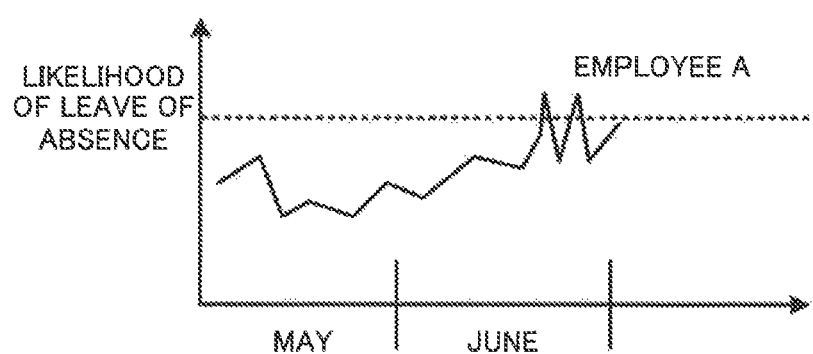
FIG. 7 illustrates an example of a graph representing variations in the likelihood of a leave of absence, output by a leave of absence prediction device in a third example embodiment of the present invention.

Subsequently, a third example embodiment of the present invention will be described. FIG. 7 is a graph representing temporal variations in the likelihood of a leave of absence, derived by a leave of absence prediction system 100 in the third example embodiment of the present invention.

The configuration of the leave of absence prediction system 100 in the present example embodiment can be the same as that of the leave of absence prediction system 100 in the first example embodiment of the present invention. The leave of absence prediction system 100 in the present example embodiment differs from the leave of absence prediction systems 100 in the first example embodiment and the like of the present invention in that the prediction unit 120 derives temporal variations in the predicted likelihood of a leave of absence. In other words, the prediction unit 120 predicts the likelihoods of a leave of absence in predetermined time at arbitrary plural time points on a daily basis, a monthly basis, or the like, and derives the results of the prediction as the history of the results of the prediction of the likelihoods of the leave of absence.

FIG. 7 is a graph representing temporal variations in the likelihood of a leave of absence, generated by the leave of absence prediction system 100 in the third example embodiment of the present invention. In the graph illustrated in FIG. 7, the horizontal axis indicates a period in which the likelihood of the leave of absence is predicted. In the graph illustrated in FIG. 7, the vertical axis indicates the degree of the likelihood of the leave of absence. In other words, the graph illustrated in FIG. 7 is a graph derived by predicting the likelihoods of the leave of absence at arbitrary plural time points by the prediction unit 120, and by plotting the results of the prediction at the plural time points described above on the horizontal axis. The graph illustrated in FIG. 7 represents that the employee may take a leave of absence, for example, when the degree of the likelihood of the leave of absence exceeds a predetermined degree indicated by the line in the direction of the horizontal axis. It is considered in the example illustrated in FIG. 7 that the likelihood of an employee A taking a leave of absence occurred in late of June.

Further, the leave of absence prediction system in the present example embodiment may derive temporal variations in the likelihoods of leaves of absence regarding plural employees, etc.

The derived temporal variations in the likelihoods of the leaves of absence, including the graph illustrated in FIG. 7, are output by any output means that is not illustrated. Examples of the output means include a display device. In such a case, the display device may be connected directly to the leave of absence prediction system 100, or may be connected to the leave of absence prediction system 100 via a communication network such as a wired or wireless communication network.

As described above, the leave of absence prediction system 100 in the present example embodiment derives the temporal variations in the predicted likelihood of a leave of absence. The derived temporal variations in the likelihood of the leave of absence are output in the form of, for example, a graph or the like which represents the variations, via any output means. Accordingly, a user of the leave of absence prediction system 100 in the present example embodiment can definitely know previous variations in the likelihood of the employees, etc. taking a leave of absence.

Fourth Example Embodiment

Figures 8, 9:
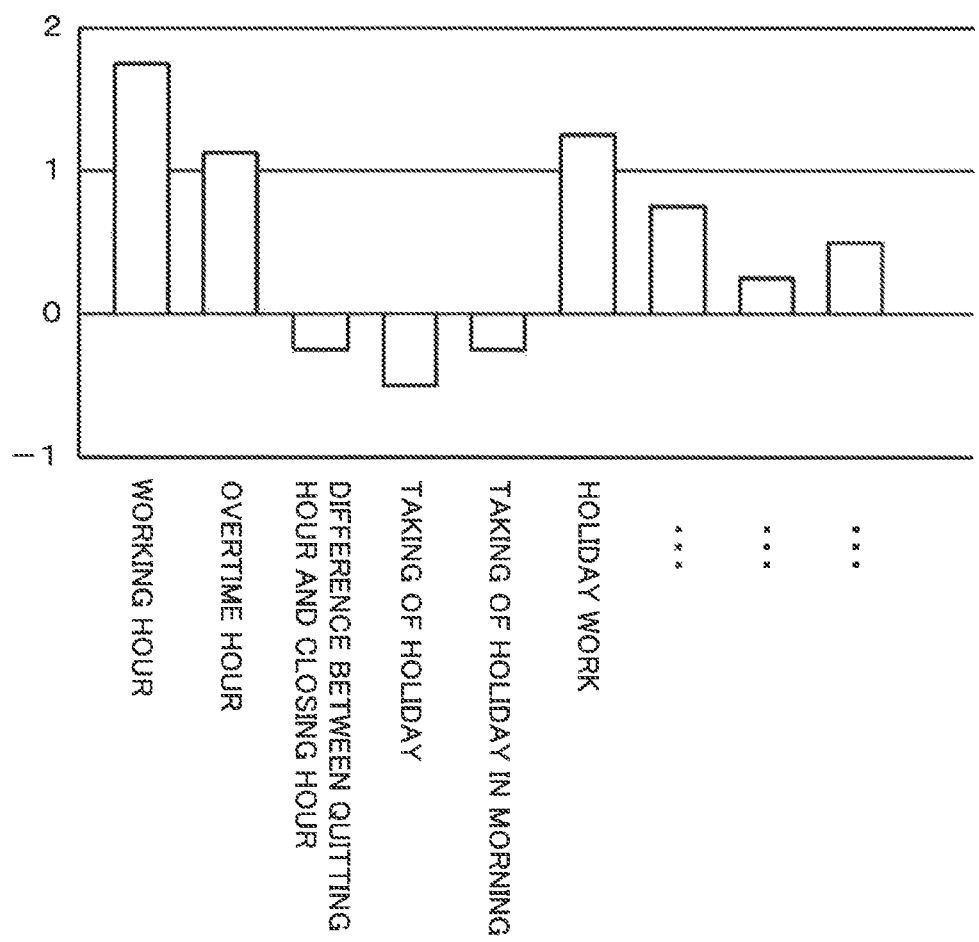
FIG. 8 illustrates an example of a table concerning the score of the likelihood of each of employees, etc. taking a leave of absence, derived in a fourth example embodiment of the present invention.
FIG. 9 illustrates an example of a graph concerning factors that may become the causes of a leave of absence, derived in a fifth example embodiment of the present invention.

Subsequently, a fourth example embodiment of the present invention will be described. FIG. 8 illustrates an example of a table concerning the score of the likelihood of each of employees, etc. taking a leave of absence, derived in the fourth example embodiment of the present invention.

The configuration of a leave of absence prediction system 100 in the present example embodiment can be the same as that of the leave of absence prediction system 100 in the first example embodiment of the present invention. In the leave of absence prediction system 100 in the present example embodiment, the prediction unit 120 derives the degrees of the likelihoods of leaves of absence predicted for plural employees.

The degrees of the likelihoods of leaves of absence concerning the plural employees, derived by the prediction unit 120, can be represented, for example, in the form of the table in FIG. 8, and the like. The table illustrated in FIG. 8 is represented in a score of which the value is increased with increasing the degree of the likelihood of a leave of absence. In other words, the table illustrated in FIG. 8 shows employees, etc. in descending order of the degree of the likelihood of a leave of absence. The table as that is output by any output means that is not illustrated, in a manner similar to that in the leave of absence prediction system 100 in the third example embodiment of the present invention. The scores listed in FIG. 8 are determined according to, for example, a distance between attendance management information and a discriminant surface for each of the employees in feature vector spaces, as described above. As an example, such a score is in a form where the score becomes a positive value when the degree of the likelihood of a leave of absence is high, and the score becomes a negative value when the degree of the likelihood of normal working is high, in accordance with the distance between the attendance management information and the discriminant surface for each of the employees. The above-described distance (d in this example) can be a from which takes a value ranges from 0 to 1 by applying to the sigmoid function $1/(1+\exp(-d))$ (exp represents the power of the base of a natural logarithm). In this case, the score becomes 1/2 when the attendance management information is on the discriminant surface in the feature vector spaces. The value approaches 1 when the degree of the likelihood of a leave of absence is high, while the value approaches zero when the degree of the likelihood of normal working is high.

As described above, the leave of absence prediction system in the present example embodiment derives the degrees of the likelihoods of leaves of absence predicted for plural employees. Accordingly, it is possible for a user of the leave of absence prediction system 100 in the present example embodiment to know an employees, etc. who is likely to take a leave of absence easily. The user of the leave of absence prediction system 100 in the present example embodiment may take action for employees, etc. with the high likelihood of a leave of absence on the basis of the derived degrees of the likelihoods of plural employees taking leaves of absence.

Fifth Example Embodiment

Subsequently, a fifth example embodiment of the present invention will be described. FIG. 9 illustrates an example of a graph concerning factors that may become the causes of a leave of absence derived in the fifth example embodiment of the present invention.

The configuration of a leave of absence prediction system 100 in the present example embodiment can be the same as that of the leave of absence prediction system 100 in the first example embodiment of the present invention. The leave of absence prediction system 100 in the present example embodiment derives a candidate for a factor causing a leave of absence when the prediction unit 120 predicts that employees, etc. as the target of prediction will be likely to take the leave of absence. The leave of absence prediction system 100 in the present example embodiment differs from the leave of absence prediction system 100 in the first example embodiment of the present invention, and the like in view of the point described above.

In the present example embodiment, the first or second attendance management information used in the leave of absence prediction system 100 includes one or more items of information regarding the attendance of an employee, etc. in a company, etc. When the first or second attendance management information includes the plural items of information concerning the attendance of the employee, etc. in the company, etc., some factors of the information regarding the attendance included in the first or second attendance management information may influence the likelihood of the leave of absence. In the leave of absence prediction system 100 in the present example embodiment, the prediction unit 120 specifies a factor that can be a cause of determination that a leave of absence is likely to be taken, and derives a candidate for the factor that is a cause of a leave of absence.

In the present example embodiment, the prediction unit 120 may specify, as a candidate for a factor causing a leave of absence, a factor concerning information satisfying predetermined conditions among items of information concerning attendance included in the second attendance management information. The prediction unit 120 may specify the candidate for the factor causing the leave of absence on the basis of a relationship between the second attendance management information and the prediction rule generated by the prediction rule learning unit 110. The prediction unit 120 may derive the candidate for the factor causing the leave of absence in any procedure other than the procedure described above.

The derived candidate for the factor causing the leave of absence is represented in the form of, for example, the graph of FIG. 9. Such a graph is output by, for example, output means that is not illustrated. The graph illustrated in FIG. 9 is output in a form in which a factor that is more likely to be a cause of the leave of absence has a higher value. In other words, employees, etc. regarding the graph illustrated in FIG. 9 are considered to be candidates for factors including working hours, overtime hours, or holiday work causing the leave of absence among causes included in the figure.

Each of the values indicated in the graph of FIG. 9 is set in relation to the discriminant described above, as described below. As an example, it is assumed that the discriminant is a linear discriminant represented in the following Equation (1).

$$f(x)=a\_0+a\_1*x\_1+a\_2*x\_2+\ldots+a\_n*x\_n \quad (1)$$

In Equation (1), $a\_0, \ldots, a\_n$ are coefficients, and x $(x\_1, \ldots x\_n)$ is a feature vector. Further, the case where $f(x)>0$ represents that employees, etc. is likely to take a leave of absence, while the case where $f(x)<0$ represents that employees, etc. works as normal. Each of $x\_1, x\_n$ corresponds to each item of the graph indicated on the horizontal axis of FIG. 9 respectively. In the example of the discriminant, the value of $a\_i*x\_i$ is corresponds to one of the factors of the graph illustrated in FIG. 9. A case where the value is positive represents that an employee, etc. is likely to take a leave of absence because of the factor. A case where the value is negative represents that the factor does not cause the employee, etc. to take a leave of absence, and that the employee, etc. is likely to work as normal.

As described above, the leave of absence prediction system 100 in the present example embodiment derives the candidate for a factor causing the leave of absence. The derived candidate for the factor causing the leave of absence is output in the form of, for example, a graph or the like via any output means. Accordingly, when there is employees, etc. who is likely to take a leave of absence, a user of the leave of absence prediction system 100 in the present example embodiment can be aware of a candidate for a factor causing the leave of absence. Therefore, it is possible for the user of the leave of absence prediction system 100 in the present example embodiment to take action for reducing the likelihood of the employees, etc. taking the leave of absence, such as exclusion of the factor causing the employees, etc. to take the leave of absence.

Sixth Example Embodiment

Figure 10:
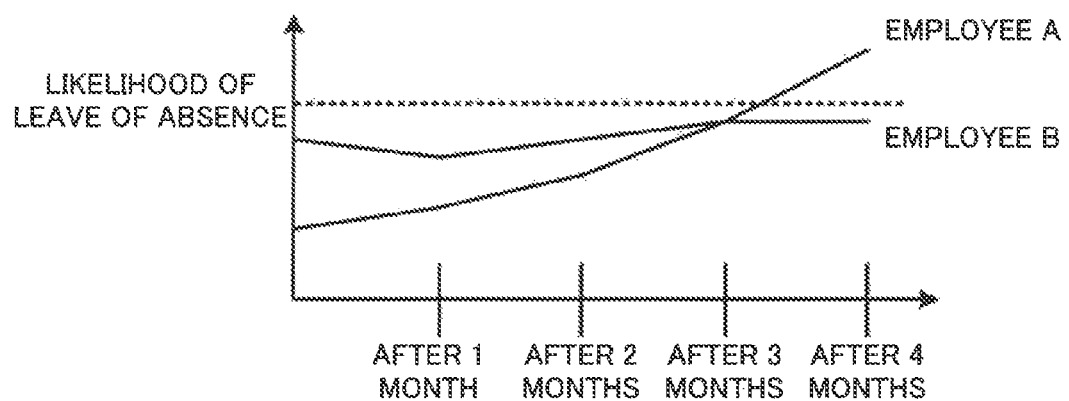
FIG. 10 illustrates an example of a graph representing variations in the likelihoods of employees, etc. taking a leave of absence, derived in a sixth example embodiment of the present invention.

Subsequently, a sixth example embodiment of the present invention will be described. FIG. 10 illustrates an example of a graph representing variations in the likelihoods of employees, etc. taking the leave of absence, derived in the sixth example embodiment of the present invention.

The configuration of the leave of absence prediction system 100 in the present example embodiment can be the same as that of the leave of absence prediction system 100 in the first example embodiment of the present invention. In the leave of absence prediction system 100 in the present example embodiment, the prediction rule learning unit 110 generates prediction rules regarding prediction of the likelihoods of employees taking leaves of absence in plural predetermined times that are different from each other. The prediction unit 120 predicts the likelihoods of employees, etc. as the target of prediction taking the leave of absence in a plurality of respective predetermined times different from each other. The leave of absence prediction system 100 in the present example embodiment differs from the leave of absence prediction system 100 in the first example embodiment of the present invention and the like in view of the points described above.

In the present example embodiment, the prediction rule learning unit 110 generates the respective prediction rules regarding the prediction of the likelihoods of the employees taking the leaves of absence in the plural predetermined times that are different from each other, as described above. In other words, the prediction rule learning unit 110 may generate the respective prediction rules in the plural predetermined times by using items of the first attendance management information with different reference dates. Further, the prediction unit 120 predicts the likelihood of the leave of absence in each of the plural predetermined times by using the respective prediction rules in the plural predetermined times, generated by the prediction rule learning unit 110.

The predicted likelihoods of leaves of absence in the plural predetermined times are represented in, for example, the graph illustrated in FIG. 10. The graph illustrated in FIG. 10 is derived by plotting the results of prediction of the likelihoods of the leaves of absence at the plural predetermined times, predicted in accordance with each of the employees, etc., with the plural time points on the horizontal axis, as an example. As illustrated in the graph illustrated in FIG. 10, the variations in the likelihoods of the employees, etc. taking the leaves of absence can be represented by predicting the likelihoods of the leaves of absence in the plural predetermined times. In the graph illustrated in FIG. 10, while the employee A has the low initial degree of the likelihood of a leave of absence, the employee A reaches, after four months, a degree that is indicated by the dotted line and that is determined to have the likelihood of a leave of absence. In contrast, while the employee B has the high initial degree of the likelihood of a leave of absence, the employee B does not reach the degree determined to have the likelihood of the leave of absence by at least four months.

Accordingly, it is possible for a user of the leave of absence prediction system 100 in the present example embodiment to take action so as not to increase degree of the likelihood of the employee A taking the leave of absence, and then to take action to decrease the degree of the likelihood of the employee B taking the leave of absence. In other words, the user of the leave of absence prediction system 100 in the present example embodiment can take action so as to prevent the employees, etc. from taking the leaves of absence in accordance with the likelihoods of the leaves of absence according to the employees, etc., the variations, and the periods in which the variations occur.

As described above, the leave of absence prediction system 100 in the present example embodiment predicts the likelihoods of leaves of absence in plural predetermined times that are different from each other. In other words, a user of the leave of absence prediction system 100 in the present example embodiment can be aware of variations in the likelihoods of employees, etc. taking leaves of absence after the time point of prediction. Accordingly, it is possible for the user of the leave of absence prediction system 100 in the present example embodiment to take action in accordance with the variations in the likelihoods of the employees, etc. taking the leaves of absence after the time point of the prediction.

The operations of the leave of absence prediction systems in the third to fifth example embodiments of the present invention can be combined with each other. The configurations of the leave of absence prediction systems in the third to fifth example embodiments of the present invention can be the same as the configuration of the leave of absence prediction system in the second example embodiment of the present invention.

The present invention has been described above with reference to the example embodiments. However, the present invention is not limited to the example embodiments described above. The constitutions and details of the present invention can be subjected to various modifications that can be understood by those skilled in the art in the scope of the present invention. The configurations in the respective example embodiments can be combined with each other unless departing from the scope of the present invention.

This application claims priority based on Japanese Patent Application No. 2014-179457, filed on Sep. 3, 2014, and the entire disclosure of which is incorporated herein in its entirety by reference.

REFERENCE SIGNS LIST

100 Leave of absence prediction system
101 Prediction rule learning device
102 Prediction device
110 Prediction rule learning unit
120 Prediction unit
130 Attendance information storage unit
140 Prediction rule storage unit
500 Information-processing device
501 CPU
502 ROM
503 RAM
504 Program
505 Storage device
506 Recording medium
507 Drive device
508 Communication interface
509 Communication network
510 Input-output interface
511 Bus

The invention claimed is:

1. A leave of absence prediction system comprising:
a processor; and
a memory storing a program executed by the processor, a first attendance management information of a first period including a time-series factor associated with employees, and information indicating presence or absence of a leave of absence in a second period following the first period, the second period being associated with each of the employees from the first period, wherein the employees include employees with leave of absence and employees with out leave of absence;

the program including steps of:
generating, by machine learning, at least one prediction model of an employee, the at least one prediction model predicting a likelihood of a leave of absence, wherein generating the at least one prediction model comprises:
obtaining feature vectors representing the first attendance management information in twelve months by calculating statistics of information concerning attendance for each month and by concatenating the calculated twelve statistics; and
learning a difference between the employees with leave of absence and the employees without leave of absence by using the feature vectors set using stochastic learning with a machine learning algorithm that uses a mathematical loss function to adjust the weights of the prediction model and on the information indicating presence or absence of the leave of absence;
predicting a likelihood of a target employee taking a leave of absence at a time corresponding to the second period, using a distance between a second attendance management information and a discriminant surface defined by the prediction model in the feature vector spaces, the second attendance management information including a time-series factor associated with the target employee; and
outputting the likelihood of the target employee taking a leave of absence at a time corresponding to the second period before the target employee takes a leave of absence.

2. The leave of absence prediction system according to claim 1, wherein
the first attendance management information includes a time-series factor over a predetermined period of time before a date, at which an employee of the employees took a leave of absence.

3. The leave of absence prediction system according to claim 1, wherein
the first attendance management information includes a time-series factor over a predetermined period of time before a date, at which an employee of the employees worked without leave of absence.

4. The leave of absence prediction system according to claim 1, wherein
the likelihood of the leave of absence represents a likelihood that a final attendance date of an employee of the employees is at a predetermined time.

5. The leave of absence prediction system according to claim 1, wherein the program further includes the steps of:
deriving a temporal variation in the predicted likelihood of the leave of absence.

6. The leave of absence prediction system according to claim 1, wherein the program further includes the steps of:
determining a degree of the likelihood of the target employee taking the leave of absence.

7. The leave of absence prediction system according to claim 1, wherein the program further includes the steps of:
deriving a candidate for a factor causing the target employee to take the leave of absence when predicting the likelihood of the target employee taking the leave of absence.

8. The leave of absence prediction system according to claim 1, wherein the program further includes the steps of:
generating the prediction model at a plurality of predetermined times that are different from each other, and performing a plurality of predictions of the likelihood of the target employee taking the leave of absence, the plurality of predictions respectively relating to a plurality of predetermined times that are different from each other.

9. The leave of absence prediction system according to claim 1, wherein
at least one of the first attendance management information or the second attendance management information includes at least one of working hours, a difference between a time of leaving an office and a time of close of business, overtime hours, situations of taking a holiday, a day of a week on which a holiday is taken, a presence or absence of holiday work, or information capable of influencing an attendance of an employee.

10. The leave of absence prediction system according to claim 1, wherein
at least one of the first attendance management information or the second attendance management information is represented as a vector obtained by concatenating a plurality of statistics in periods, and
the statistics is calculated from at least one of an average of working ours, an average of differences between a time of leaving an office and a time of close of business, or an average of numbers of taken holidays.

11. The leave of absence prediction system according to claim 1, wherein the first attendance management information includes both attendance management information for the employees without leave of absence and attendance management information for the employees with leave of absence.

12. A prediction rule learning device comprising:
a processor; and
a memory storing a program executed by the processor, a first attendance management information of a first period including a time-series factor associated with employees, and information indicating presence or absence of a leave of absence in a second period following the first period, the second period being associated with each of the employees from the first period, wherein the employees include employees with leave of absence and employees without leave of absence;
the program including steps of:
generating, by machine learning, at least one prediction model of an employee, the at least one prediction model predicting a likelihood of a leave of absence, wherein generating the at least one prediction model comprises:
obtaining feature vectors representing the first attendance management information in twelve months by calculating statistics of information concerning attendance for each month and by concatenating the calculated twelve statistics; and
learning a difference between the employees with leave of absence and the employees without leave of absence by using the feature vectors set using stochastic learning with a machine learning algorithm that uses a mathematical loss function to adjust the weights of the prediction model and on the information indicating presence or absence of the leave of absence;
predicting a likelihood of a target employee taking a leave of absence at a time corresponding to the second period, using a distance between a second attendance management information and a discriminant surface defined by the prediction model in the feature vector spaces, the second attendance management information including a time-series factor associated with the target employee; and
outputting the likelihood of the target employee taking a leave of absence at a time corresponding to the second period before the target employee takes a leave of absence.

13. A prediction device comprising:
a processor; and
a memory storing a program executed by the processor, the program including steps of:
predicting a likelihood of a target employee taking a leave of absence based on a distance between a second attendance management information and a discriminant surface defined by a prediction model in feature vector spaces, the second attendance management information including a time-series factor associated with the target employee, wherein:
the prediction model predicts a likelihood of a leave of absence, and
the prediction model is generated by:
obtaining feature vectors representing a first attendance management information in twelve months by calculating statistics of information concerning attendance for each month and by concatenating the calculated twelve statistics; and
learning a difference between employees with leave of absence and employees without leave of absence by using the feature vectors set using stochastic learning with a machine learning algorithm that uses a mathematical loss function to adjust the weights of the prediction models and on an information indicating presence or absence of leave of absence; and
outputting the likelihood of the target employee taking a leave of absence at a time corresponding to the second period before the target employee takes a leave of absence.

14. A leave of absence prediction method comprising:
storing a first attendance management information including a time-series factor associated with employees in a first period, and information indicating presence or absence of a leave of absence associated with each of the employees in a second period following the first period, the second period being associated with each of the employees from the first period, wherein the employees include employees with leave of absence and employees without leave of absence;
generating, by machine learning, at least one prediction model of an employee, the at least one prediction model predicting a likelihood of a leave of absence, wherein generating the at least one prediction model comprises:
obtaining feature vectors representing the first attendance management information in twelve months by calculating statistics of information concerning attendance for each month and by concatenating the calculated twelve statistics; and
learning a difference between the employees with leave of absence and the employees without leave of absence by using the feature vectors set using stochastic learning with a machine learning algorithm that uses a mathematical loss function to adjust the weights of the prediction model and on the information indicating presence or absence of the leave of absence;
predicting a likelihood of a target employee taking a leave of absence at a time corresponding to the second period, using a distance between a second attendance management information and a discriminant surface defined by the prediction model in the feature vector spaces, the second attendance management information including a time-series factor associated with the target employee; and outputting the likelihood of the target employee taking a leave of absence at a time corresponding to the second period before the target employee takes a leave of absence.

15. A computer-readable non-transitory recording medium storing a program that causes a computer to execute the processes of:

storing a first attendance management information including a time-series factor associated with employees in a first period, and information indicating presence or absence of a leave of absence associated with each of the employees in a second period following the first period, the second period being associated with each of the employees from the first period, wherein the employees include employees with leave of absence and employees without leave of absence;

generating, by machine learning, at least one prediction model of an employee, the at least one prediction model predicting a likelihood of a leave of absence, wherein generating the at least one prediction model comprises:

obtaining feature vectors representing the first attendance management information in twelve months by calculating statistics of information concerning attendance for each month and by concatenating the calculated twelve statistics; and learning a difference between the employees with leave of absence and the employees without leave of absence by using the feature vectors set using stochastic learning with a machine learning algorithm that uses a mathematical loss function to adjust the weights of the prediction model and on the information indicating presence or absence of the leave of absence;

predicting a likelihood of a target employee taking a leave of absence at a time corresponding to the second period, using a distance between a second attendance management information and a discriminant surface defined by the prediction model in the feature vector spaces, the second attendance management information including a time-series factor associated with the target employee; and outputting the likelihood of the target employee taking a leave of absence at a time corresponding to the second period before the target employee takes a leave of absence.

* * * * *